United States Patent [19]

Bowers-Irons et al.

[11] Patent Number: 5,030,425

[45] Date of Patent: * Jul. 9, 1991

[54] BIODEGRADATION AND RECOVERY OF GALLIUM AND OTHER METALS FROM INTEGRATED CIRCUITS

[75] Inventors: Gail L. A. Bowers-Irons, Salt Lake City; John R. Pease, Kearns, both of Utah

[73] Assignee: Technical Research, Inc., Salt Lake City, Utah

[*] Notice: The portion of the term of this patent subsequent to Jul. 9, 2008 has been disclaimed.

[21] Appl. No.: 372,058

[22] Filed: Jun. 27, 1989

[51] Int. Cl.$^5$ .............. C22B 30/04; C22B 13/00; C22B 25/00; C22B 41/00

[52] U.S. Cl. .................... 423/87; 423/98; 423/109; 423/131; 435/262

[58] Field of Search .............. 423/131, DIG. 17, 98, 423/87, 109; 75/101 R, 121, 743; 435/262

[56] References Cited

U.S. PATENT DOCUMENTS

| | | | |
|---|---|---|---|
| 3,272,621 | 9/1966 | Zajic | 423/DIG. 17 |
| 3,305,353 | 2/1967 | Duncan | 75/101 R |
| 3,679,397 | 7/1972 | O'Connor | 423/DIG. 17 |
| 4,497,778 | 2/1985 | Pooley | 423/131 |
| 4,571,387 | 2/1986 | Bruynesteyn et al. | 435/262 |
| 4,728,082 | 3/1988 | Emmett, Jr. et al. | 266/168 |
| 4,732,608 | 3/1988 | Emmett, Jr. et al. | 75/101 R |
| 4,758,345 | 7/1988 | Francis et al. | 210/611 |

OTHER PUBLICATIONS

Use of Micro-Organisms for the Recovery of Metals by Tuovinen and Kelly, International Metallurgical Reviews, vol. 19, 1974.

"Bioaccumulation of Germanium by *Pseudomonas putida* in the Presence of Two Selected Substrates" by Chmielowski, *Appl. and Envir. Micro.*, May 1986, pp. 1099-1103.

*The Bacterial Leaching of Metals from Ores* by Karaivko et al. (Technicopy Ltd., 1977).

"Bacterial Leaching" by C. Brierley (CRC Critical Reviews in Microbiology, Nov. 1978).

"Analytical Chemistry of Gallium" by Dymov and Sarostin (Ann Arbor Science Publishers, 1970).

"Acid-Bacterial and Ferric Sulfate Leaching of Pyrite Single Crystals" by Keller et al. (24 Biotech. and Bioeng., 1982, pp. 83-96).

"Studies on the Chemoautotrophic Iron Bacterium Ferrobacillus Ferrooxidans" by Silverman et al., 1959.

"Kinetics of Bio-chemical Leaching of Sphalerite Concentrate" by Chaudhury et al. (16B Metallurgical Transactions, 12/85, pp. 667-670).

"Microorganisms in Reclamation of Metals" by Hutchins et al. (40 Ann. Rev. Microbiol. 1986, pp. 311-336).

"Oxidation of Gallium Sulfides by *Thiobacillus Ferrooxidans*" by A. Torma (24 Dan. J. Microbiol. 1978, pp. 888-891).

"Biological Leaching: A New Method for Metal Recovery" (B.C. Research; Vancouver, B.C.).

"Ore Leaching by Bacteria" by Lundgren et al. (34 Ann. Rev. Microbiol. 1980, pp. 263-283).

"Continuous Bacterial Coal Desulfurization Employing *Thiobacillus Ferrooxidans*" by Myerson et al. (26 Biotech. and Bioeng. 1984, pp. 92-99).

(List continued on next page.)

Primary Examiner—Michael L. Lewis
Assistant Examiner—Steven Bos
Attorney, Agent, or Firm—Trask, Britt & Rossa

[57] ABSTRACT

Disclosed is a process for leaching selected metal compounds (e.g. gallium arsenide) from integrated circuits containing those compounds. The method includes placing the integrated circuits into a culture medium containing bacteria. Bacteria capable of leaching the metal compounds from the integrated circuits leach the metals from the integrated circuits. The bacteria preferably used will be ATCC 53921 and mutations and recombinants thereof. The integrated circuits are generally crushed to between 20 and −400 mesh before placement into the culture medium containing bacteria.

10 Claims, 5 Drawing Sheets

OTHER PUBLICATIONS

"Development of a Continuous Process for Metal Accumulation by *Zoogloea ramigera*" by Norber et al. (26 Biotech. and Bioeng., 1984, pp. 265-268).

"Biosorption of Uranium and Lead by *Streptomyces Longwoodensis*" by Friis et al. (28 Biotech. and Bioeng., 1986, pp. 21-28).

"Accumulation of Heavy-Metal Ions by *Zoogloea ramigera*" by Norberg et al. (26 Biotech. and Bioeng., 1984, pp. 239-246).

"Microbiological Mining" by C. L. Brierly (1982).

"Wastewater Engineering: Treatment, Disposal, Reuse" (McGraw-Hill; 2nd Edition, pp. 494-497).

"Biologically Mediated Inconsistencies in Aeration Equipment Performance" by Albertson et al. (47 Jr. W.P.C.F. No. 5, May 1975, pp. 976-988).

The Dorco Technical Manual, Sec. 32, Dec. 1951.

"The Separation of Gallium and Its Colorimetric Determination by Means of Quinalizarin" by H. Willard et al. (1937).

The Chemistry of Gallium by Sheka et al. (Elsevier Publishing Co. 1966).

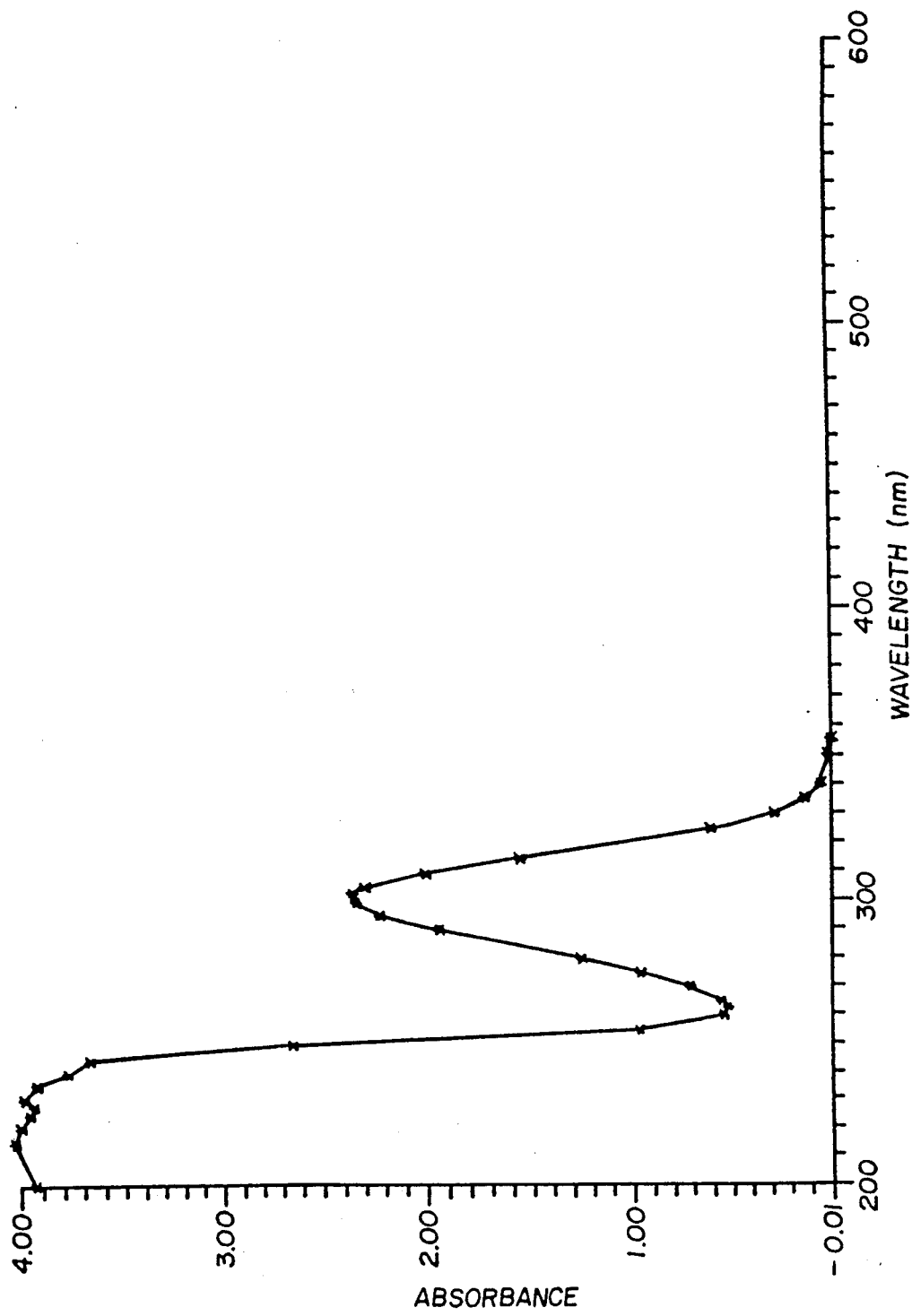

BIODEGRADATION AND RECOVERY OF GALLIUM AND OTHER METALS FROM INTEGRATED CIRCUITS

This invention was made with Government support under Contract No. F33615-87-C-5303 awarded by the United States Air Force. The Government has certain rights in this invention.

BACKGROUND OF THE INVENTION

1. Field

This invention is directed to a biological process for use in removing valuable metallic components from a conglomeration of other materials by biological techniques. The invention is more particularly directed to the extraction of gallium or germanium from gallium or germanium containing integrated circuits by the use of a "bioleaching" technique.

2. State of the Art

Gallium arsenide (GaAs) is used as a semiconductor in integrated circuits ("chips"). Chips containing GaAs have achieved operating speeds of up to five times that of the fastest silicon chips. The GaAs chips also operate at a wider temperature range than silicon circuits.

However gallium arsenide does have some drawbacks. Arsenic is volatile and toxic. Gallium is relatively expensive (twenty times the price of aluminum on a weight basis).

Even with the relatively high cost of GaAs chips, they have been discarded when defective or damaged. Chemically extracting GaAs from chips has been prohibitively expensive, and extraction is possibly dangerous due to the presence of arsenic.

Accordingly, it would be an improvement in the art if a relatively low cost, efficient way of extracting gallium arsenide from "rejected" or damaged chips existed.

Similarly, there has been an increased use of germanium in integrated circuitry chips, and it is clear that a process for recovering germanium from this source would also be an improvement in the art.

As reported in Lundgren et al., "Ore Leaching by Bacteria," *Ann. Rev. Microbial,* 34: 63-83 (1980), Thiobacillus ferrooxidans has been used to oxidize gallium sulfide ($Ga_2S_3$) to gallium sulfate ($Ga_2(SO_4)_3$). Torma, in "Oxidation of gallium sulfides by *Thiobacillus ferrooxidans*", *Can J. Microbial,* 24: 888-891 (1978), disclosed a method for biomining/bioleaching/biostabilization by bacterium involving inoculating a quantity of gallium-bearing chalcopyrite concentrate and 70 ml iron-free nutrient medium with prepared *Th. ferrooxidans.* The system is aerated with carbon dioxide ($CO_2$)-containing air. Distilled water is added to compensate for evaporation, and the pH is maintained at 1.8. The temperature of the reaction is typically 35° C.

*The Bacterial Leaching of Metals From Ores,* written by G. I. Karaivko, et al. and published in 1977, discusses the use of *Thiobacillus ferrooxidans* in leaching non-ferrous metals and sulfides. This article notes that *Th. ferrooxidans* may be used to leach rare metals such as gallium from the crystal structure of many sulfides and non-ferrous metals. The authors suggest a methodology for leaching non-ferrous metals in vats using *Th. ferrooxidans.* The method emphasizes the need for proper aeration, optimal mesh size of ore, pH at about 2.8, and a suggested reaction temperature of approximately room temperature (26° C.).

These and other writings indicate an established study of bioleaching of iron- and sulfur-containing ores, but investigation has been done almost exclusively through the use of Thiobacillus species, particularly *Th. ferrooxidans.*

For example, bioleaching of copper from chalcopyrite containing ore is described in U.S. Pat. No. 4,571,387 to Bruynsteyn, et al. the contents of which are hereby incorporated by this reference. This patent discloses a process for leaching particular metals from ores using sulfide oxidizing bacteria.

The publication "Analytical Chemistry of Gallium" by Dymov and Sarostin (Ann Arbor Science Publishers, 1970) discusses the characteristics and properties of gallium, and discusses various methods of extracting gallium including electrical extraction, chromatography, and the use of organic solutions.

"Acid-Bacterial and Ferric Sulfate Leaching of Pyrite Single Crystals" by Keller, et al. (24 (*Biotech. and Bioeng.,* 1982 pp. 83-96) discusses use of *Th. ferrooxidans* to leach pyrite crystals.

"Studies on the Chemoautotrophic Iron Bacterium *Ferrobacillus ferrooxidans*" by Silverman, et al. (1959) discusses a method for culturing chemoautotrophic bacterium such as Gallionella, *Th. ferrooxidans,* and *F. ferrooxidans.*

"Microorganisms in Reclamation of Metals" by Hutchins, et al. (40 *Ann. Rev. Microbiol.* 1986, pp. 311-36), describes various methods of leaching metals from ores using acidophilic iron-oxidizing bacteria. Hutchins further discusses the characteristics of many bacterial forms capable of effectuating bioleaching. Reference is made to bioleaching of $Ga_2S_3$ by *T. ferrooxidans.*

"Biological Leaching: A New Method For Metal Recovery" (B.C. Research; Vancouver, B.C.) provides a general discussion of bioleaching of sulfides in industrial and commercial applications.

"Ore Leaching By Bacteria" by Lundgren, et al. (34 *Ann. Rev. Microbiol.* 1980, pp. 263-83) details the chemical mechanisms of bioleaching metals from insoluble minerals.

"Bacterial Leaching" by C. Brierley (*CRC Critical Reviews in Microbiology,* November 1978) discusses industrial applications of bioleaching, with particular emphasis on uranium and copper recovery. Details are provided regarding bacterial efficacy parameters.

"Continuous Bacterial Coal Desulfurization Employing *Thiobacillus Ferrooxidans*" by Myerson, et al. (26 *Biotech. and Bioeng.* 1984, pp. 92-99) discusses the increase in bioleaching activity with increase in surface substrate availability.

"Microbiological Mining" by C. L. Brierly (1982) discusses the role played by *T. ferrooxidans* in leaching copper from low-grade ore on an industrial scale.

"Wastewater Engineering: Treatment, Disposal, Reuse" (McGraw-Hill; 2nd Edition, pp. 494-497) discloses methods and apparatus for aeration of biological systems.

"Biologically Mediated Inconsistencies in Aeration Equipment Performance" by Albertson, et al. (47 *Jr. W.P.C.F.* No. 5, May 1975, pp. 976-988) provides an evaluation of aeration devices used in biological systems.

The Dorrco Technical Manual, Sec. 32, describes the operation of an agitator - slurry mixer.

"The Bacterial Leaching of Metals from Ores" by Karaivko, et al. (Technicopy Limited, 1977) provides a treatise on bioleaching methodologies, and makes reference to the aqueous migration of gallium in relation to pH values in bioleaching processes.

SUMMARY OF THE INVENTION

The invention includes a biological process for leaching selected metal compounds from a conglomeration of materials, especially manufactured components such as integrated circuits, containing those compounds. The method involves comminuting or crushing the integrated circuits and placing the crushed integrated circuits into a culture media containing selected bacteria. The selected bacteria are capable of leaching the metal compounds from the integrated circuits. The process requires an amount of time sufficient to allow the bacteria to leach the metals from the integrated circuits. Generally, the process is used to leach metal compounds, a metallic component of which is gallium or germanium.

The bacteria may be a mixture of different species of bacteria. Bacteria which is preferably used is that deposited with ATCC and is identified as ATCC Deposit No. 53921 or mutations or recombinants thereof. The organisms denominated as ATCC 53921 differ from Thiobacillus and other species which have been used in other bioleaching processes. Bacteria ATCC 53921 consist of a mixed culture of substantially rounded forms at most temperatures, exhibit a greater affinity for gallium and germanium, exhibit an affinity for arsenic, operate at lower pH valves, and operate at a wider range of temperatures (room temperature to 90° C.). Bacteria ATCC 53921 also solubilizes tin and lead solder which may be associated with the integrated circuits. In contrast, *Thiobacillus ferrooxidans* is generally unaffected by the presence of copper, which exhibits a "poisoning" effect on bacteria ATCC 53921.

The integrated circuits used herein are generally "scrap". They are generally crushed to between 20 and −400 mesh, although they need not be crushed at all. All references to mesh, unless otherwise denominated, are to "Tyler mesh." The process is typically conducted at a temperature of about 25° to about 85° centigrade and at a pH of between 1.0 and 2.5. Gallium arsenide is relatively more soluble at higher temperatures (e.g. >45° C. in aqueous media), and the process is more effective at higher temperatures.

Air containing oxygen, carbon dioxide or combinations thereof may be diffused or sparged through the culture media, bacteria, and crushed integrated circuits, although this step is not essential to the practice of the invention.

In an alternative embodiment of the invention, the bacteria is a recombinant bacteria containing DNA derived from bacteria of ATCC 53921 or mutations thereof. In another alternative embodiment, the bacteria used to process the comminuted integrated circuits contains DNA derived from ATCC 53921.

BRIEF DESCRIPTION OF THE FIGURES

FIG. 5 is a spectroanalysis of gallium standard at 1000 ppm, Aesar 88066.

DETAILED DESCRIPTION OF THE PREFERRED EMBODIMENTS

Figure 1:
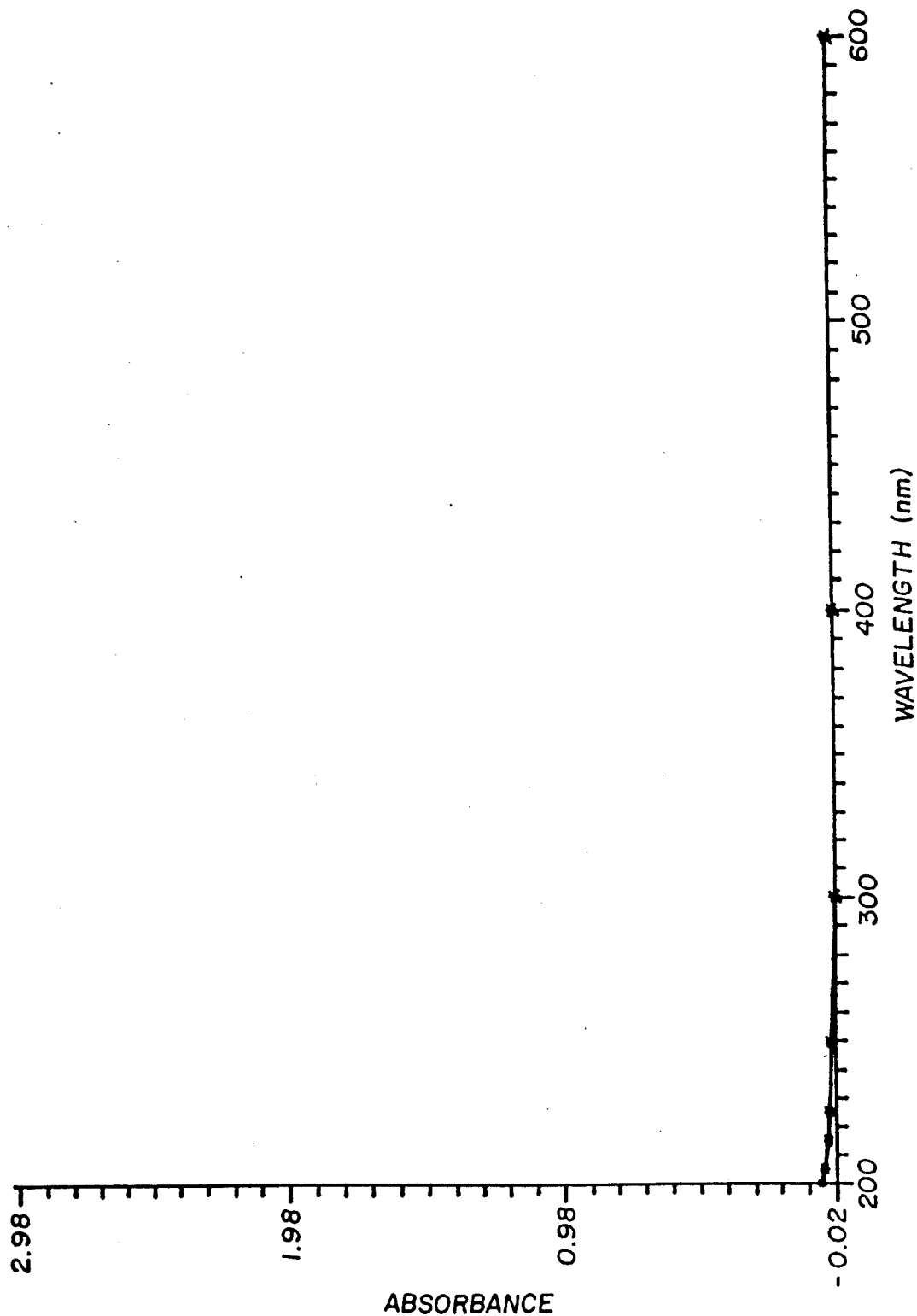
FIG. 1 is a spectroanalysis of a sample of integrated circuitry (chip) degradation in which no bacteria were added (Example C)
Figure 2:
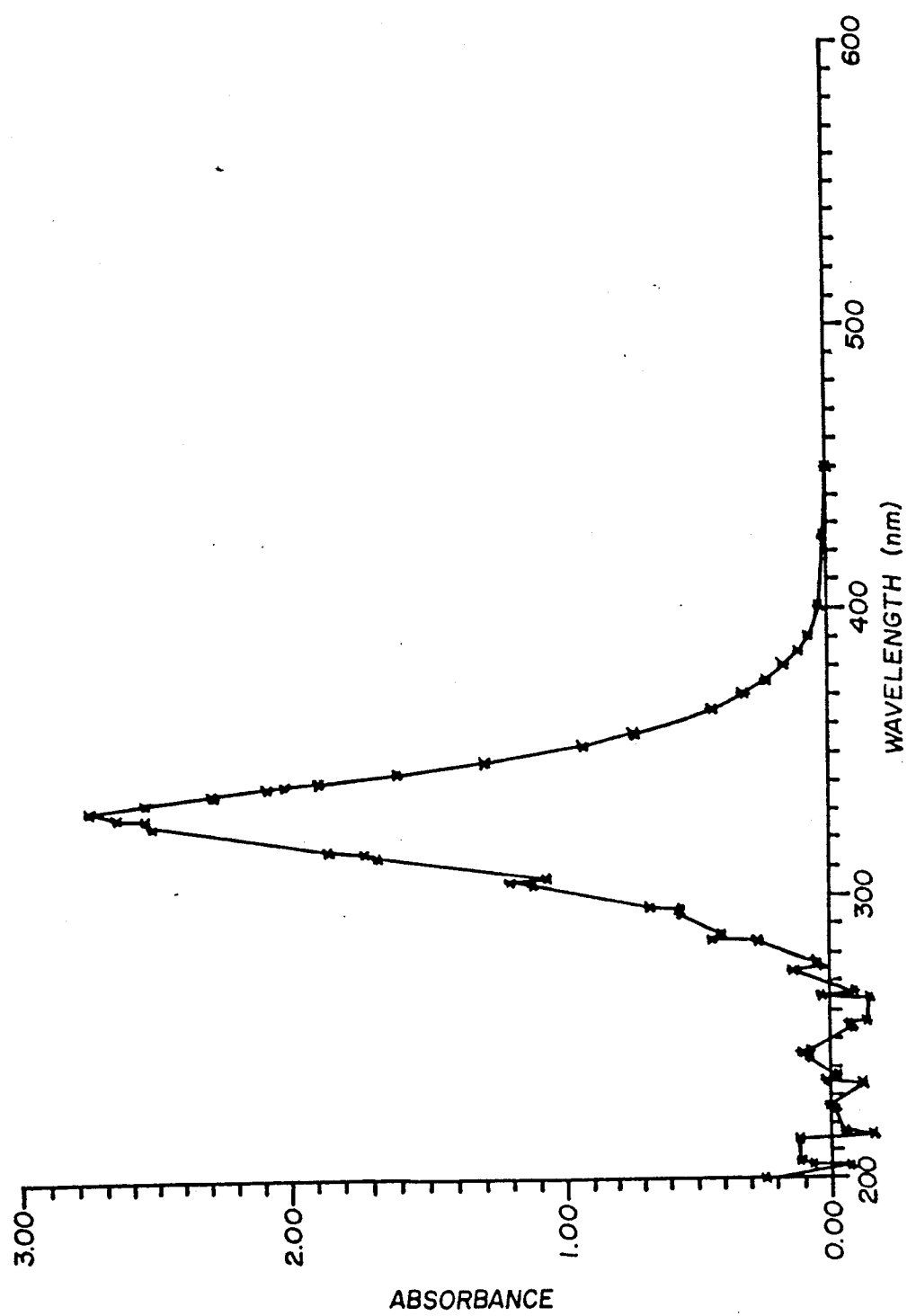
FIG. 2 is a spectroanalysis following degradation of a sample of integrated circuitry (chip) at 500 ppm.
Figure 3:
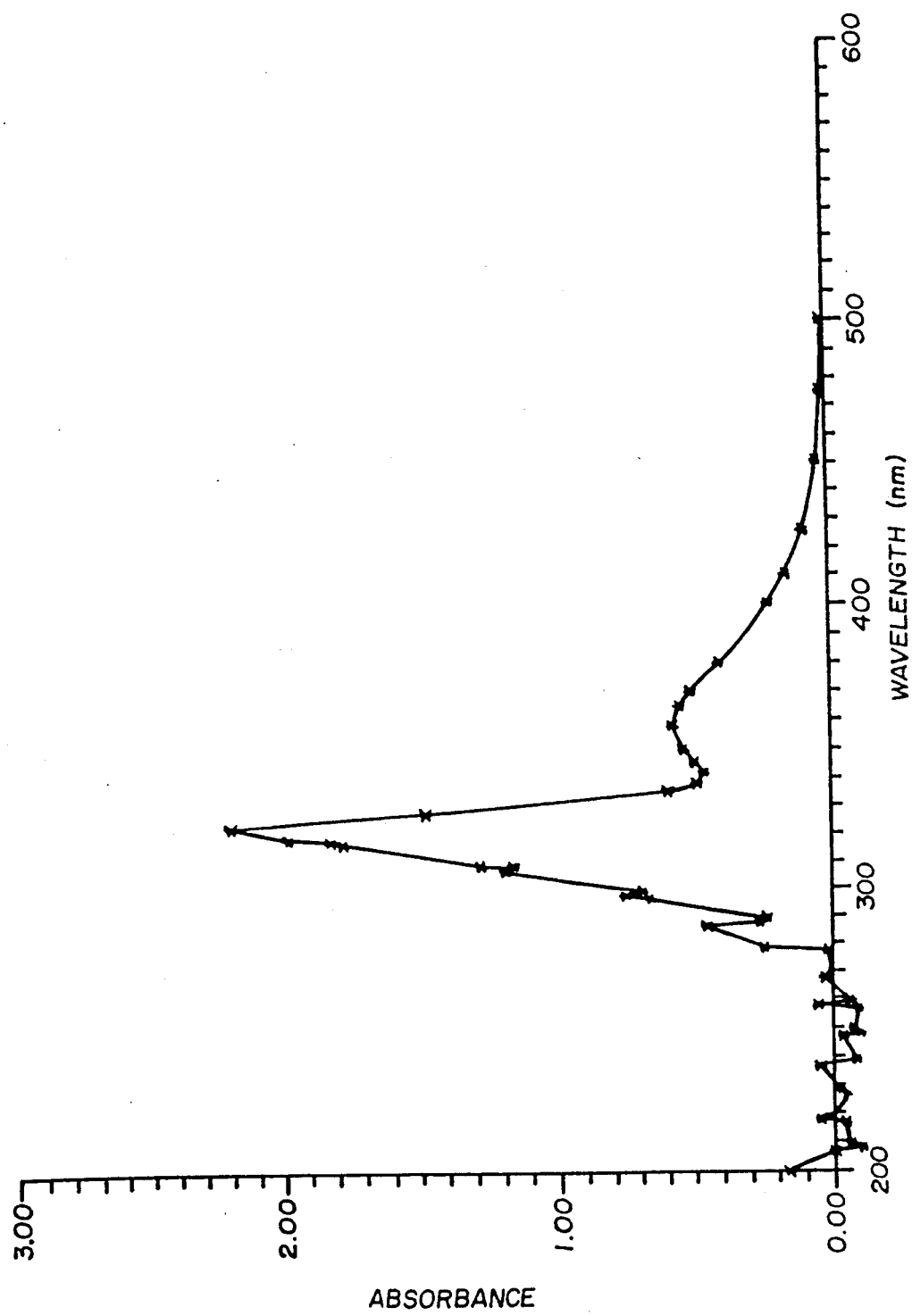
FIG. 3 is a spectroanalysis of gallium arsenide standard 200 ppm Aesar 12934C, 99–99.9% (Examples A–C)
Figure 4:
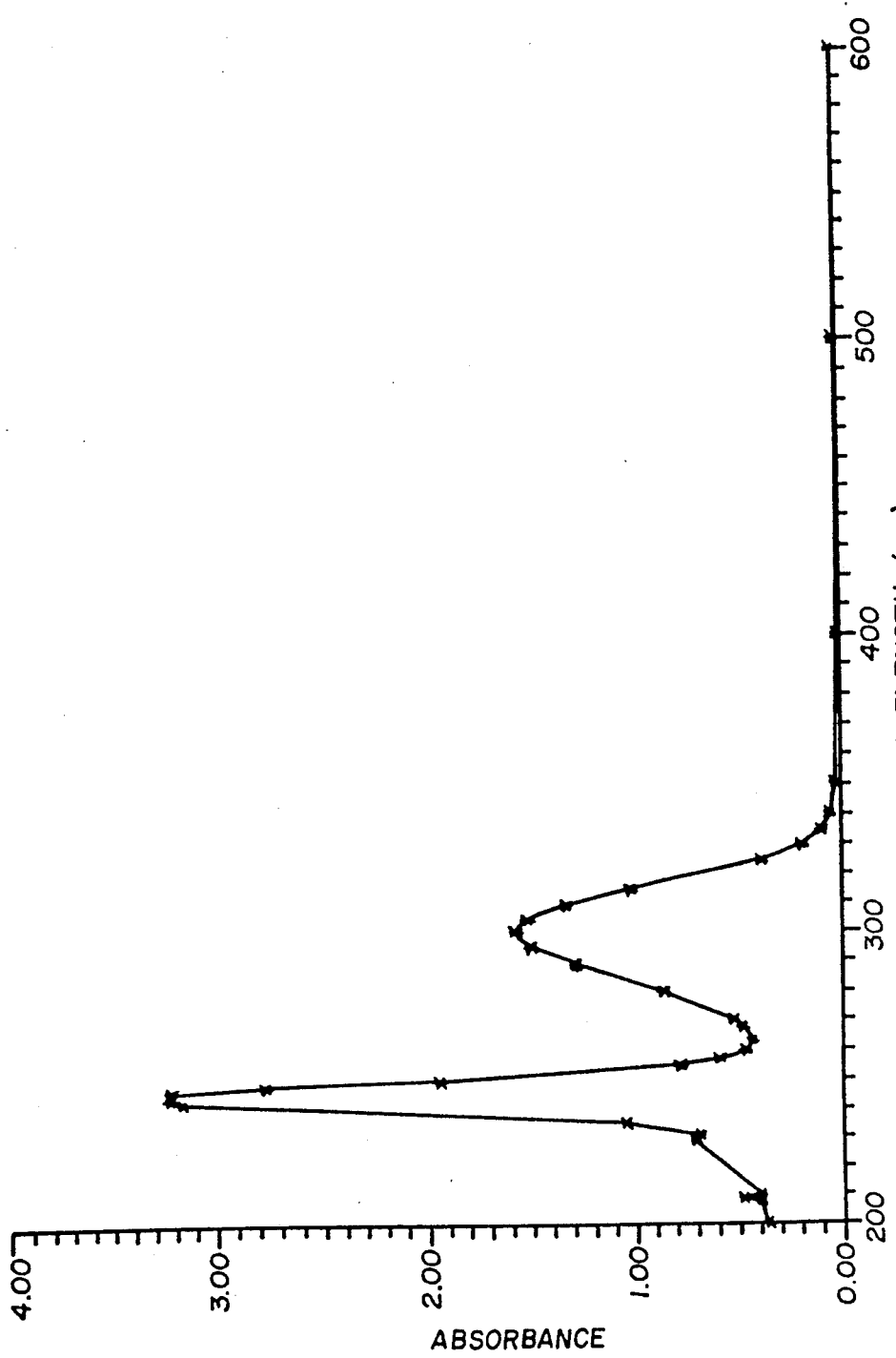
FIG. 4 is a spectroanalysis of gallium solubilization following purification (Examples A–C)

Bacteria capable of bioleaching gallium arsenide and other metals can be naturally occurring. Such strains of bacteria should be common, naturally occurring, and readily discoverable. Typically such strains would be thermophilic or mesophilic microorganisms. Thermophilic microorganisms are widely distributed in soils, self-heated hays, and geothermally heated areas (e.g. tectonically active areas of the earth, sulfatara fields, and geothermal power plants). Mesophiles are also widely distributed throughout nature.

Once a source of mesophiles has been identified, various strains of the bacteria can be isolated using well-known techniques. For example, the bacteria may be streaked onto a sterile glass petri dish containing solid or semi-solid nutrient medium. This medium contains nutrients which the bacteria can use as food.

Within a few days, the various bacterial cells should reproduce covering the medium with colonies of bacteria. Assuming individual cells were well separated in the initial streaking, isolated colonies will have arisen from a single bacterium and will therefore be composed of many identical organisms.

If such a colony is touched with a sterile needle and the adhering cells transferred to another sterilized medium, the bacteria will reproduce as a pure culture (a culture composed of one kind of bacterium).

Other well-known pure culture techniques such as "streak-plate" or "pour-plate" (Example D) methods may be used to obtain pure cultures. The bacteria may also be sustained on a liquid medium such as infusion media. Infusion media is especially preferred for use with thermophilic bacteria due to the temperatures involved.

Preferably the medium will contain gallium arsenide. In such a case, the medium can be used as a preliminary screening step to determine if the bacteria is capable of bioleaching gallium arsenide from chips. In the case of ATCC 53921, the concentration of GaAs in the medium will not exceed 13 weight percent.

Once the bacteria has been isolated into a pure culture, and preliminarily screened with GaAs containing medium, the bacteria can be further screened to determine whether or not it can be used to bioleach the gallium or germanium from the integrated circuits. One such screening technique is to incorporate the isolated bacteria into the processes of the hereinafter described Examples A–C and then analyze the culture medium for the presence of the desired metal component.

A preferred bacteria for use in the instant invention is one deposited with ATCC which bears ATCC Deposit No. 53921. Bacteria ATCC 53921, believed to be a mixed culture of bacteria, was deposited with the American Type Culture Collection, 12301 Parklawn Drive, Rockville, Md. 20852, USA, under the Budapest Treaty on June 26, 1989. This bacteria bioleaches gallium arsenide at temperatures ranging from 15° C. to 90° C. Temperatures above 45° C. are preferred. At 62° C. the rate of bioleaching is five times faster than at room temperature. Generally, the greater the temperature, the greater the speed of the bioleaching.

"Mutants" as used herein refer to bacteria which have mutated, either naturally, or by inducement. "Recombinants" as used herein refer to recipient cell forms into which the genetic material of a donor cell (e.g. ATCC 53921) has been placed. Processes for inducing mutations and creating recombinants can be found in various publications, such as Watson et al. *The Molecular Biology of the Gene*, Vol. 1 3–585 (W. A. Benjamin, Menlo Park, Calif. 4th ed. 1987) (mutations), Beers et al. *Cell Fusion: Gene Transfer and Transformation*, pp. 79–275 (Raven Press 1984); Denniston et al., *Recombinant DNA*, pp. 109–290 (Bowbin, Hutchinson, Strasburg, Pa. 1981); Chafer et al. *Genetic Rearrangement*, pp. 59–74 (Sinauer Assoc. 1980); and Kushev, *Mechanisms of Genetic Recombination*, pp. 5–175 (Consultants Bureau 1974) the contents of all of which are incorporated by this reference.

The integrated circuits ("chips") containing the gallium arsenide, germanium compound, or other desired metal compound are preferably first crushed, comminuted or otherwise broken down into smaller pieces or particles. Alternatively, whole chips may be used. Generally the smaller the size of the crushed circuits the greater the amount of desired metal compound extractable during the process.

The chips are then placed into a container containing culture medium inoculated with a bacteria capable of extracting the desired metal compound, such as ATCC No. 53921 bacteria. A concentration of bacteria sufficient to leach the metal compounds (e.g. 5 cc of existing culture ATCC 53921 may be added to 200 ml 9K with gallium containing chips) should be present in the culture medium, although the bacteria will eventually multiply in suitable culture medium to sufficient numbers to achieve bioleaching. ATCC 53921 generally attaches to the crushed gallium arsenide chips immediately. Gallium arsenide dissolves into the culture medium, along with lead and tin solder.

The particular culture medium containing the bacteria and crushed chips is preferably mixed during the bioleaching process. A magnetic bar stirrer works ideally. Such mixing or agitation increases the gallium arsenide distribution throughout the solution. Rotary mixing of the mixture may be used but is not as effective as magnetic bar stirring.

After the desired metal compound has been extracted from the chips and dissolved into the culture medium, the culture medium is filtered or otherwise separated from the other constituents.

The gallium arsenide is then recovered from the culture medium using one of several known extraction techniques (e.g. ion exchange, biosorption, accumulation, or bioaccumulation). See, e.g. "Development of a Continuous Process for Metal Accumulation by *Zoogloea ramigera*" by Norber, et al. (26 *Biotech and Bioeng.* 1984, pp. 265–68) which discusses bioaccumulation of metals from aqueous solutions; "Biosorption of Uranium and Lead by *Streptomyces Longwoodensis*" by Friis, et al. (28 *Biotech and Bioeng.* 1986, pp.21–28) which discusses the recovery of heavy metals through the mechanism of biosorption; "Accumulation of Heavy-Metal Ions by *Zoogloea ramigera*" by Norberg, et al. (26 *Biotech. and Bioeng.* 1984, pp. 239–46) which describes a method for accumulation of metals from effluent solutions using bacteria; "Bioaccumulation of Germanium by *Pseudomonas putida* in the Presence of Two Selected Substrates" by Chmielowski, et al. (*Applied and Envir. Microbiology*, May 1986, pp. 1099–1103) which discusses the recovery of Ge from the wastewaters of coke technology by bioaccumulation; the chemistry and detection of gallium using colorimetric methodology is disclosed in "The Separation of Gallium and its Colorimetric Determination by Means of Quinalizarin" by H. Willard, et al (1937); and "*The Chemistry of Gallium*" by Sheka, et al. (Elsevier Publishing Co. 1966) presents a compendium of gallium chemistry, and discusses the recovery of gallium in the aluminum industry using solution leaching processes and other methods. The contents of these references are hereby incorporated by this reference.

Bacteria, such as ATCC 53921, may be placed in the following media: ATCC-B, ATCC-D, Nutrient Broth, Tryptone Glucose Extract, Potato Dextrose, Lundgren's 9K and Silica Gel. Such media were prepared with 0.2 μm Nanopure TM purified water in 500 or 1000 ml volumetric flasks. After diluting to volume, the flasks were heated slowly on a Corning hot/stir plate while stirring. After the ingredients were in solution or well dispersed, the media, excluding 9K, were autoclaved. The 1000 ml solutions were poured into 500 ml flasks due to autoclave size limitations. The flasks were autoclaved at 121° C./15 psi (pounds per square inch) for 20 minutes. Initial autoclaving was completed in 20 minutes. Sterilization times exceeding 15 minutes are preferred.

Typical formulations of such mixtures are:

A. ATCC-B

| Nutrient | % |
| --- | --- |
| Yeast Extract | 0.40 |
| Starch | 0.50 |
| Magnesium Sulfate | 0.05 |
| Potassium Dihydrogen Phosphate | 0.10 |
| Ammonium Nitrate | 0.10 |
| Sodium Chloride | 0.01 |
| If used for plates: | |
| Agar | 1.75 |

The solutions were pH adjusted to 5.5 with 1.0N $H_2SO_4$ and autoclaved.

B. Nutrient Broth

| Nutrient | % |
| --- | --- |
| Beef Extract | 0.30 |
| Peptone | 0.50 |
| If used for plates: | |
| Agar | 1.75 |

The solution was then diluted to volume, pH adjusted to 7.0 and autoclaved.

C. Tryptone Glucose Extract (TGE)

| Nutrient | % |
| --- | --- |
| Beef Extract | 0.30 |
| Tryptone | 0.50 |
| Glucuse (Dextrose) | 0.10 |
| If used for plates: | |
| Agar | 1.75 |

The solution was then diluted to volume, pH adjusted to 7.0 and autoclaved.

D. Potato Dextrose

| Nutrient | % |
| --- | --- |
| Potatoes | 30.00 |
| Dextrose | 2.00 |
| If used for plates: | |
| Agar | 1.75 |

Diced potatoes were boiled in water until thoroughly cooked. The liquid and solids were then filtered through cheese cloth. The filtrate was placed in a volumetric flask with 2% dextrose diluted to volume and autoclaved. The solution was not pH adjusted and was used only for culture isolation.

E. 9K

ATCC 53921 was also maintained in Lundgren's 9K nutrient. This is the preferred culture medium. This pH 1.8 nutrient solution is a sterile filtered mixture of the following materials:

| Nutrient | Grams per Liter |
| --- | --- |
| Ammonium Phosphate | 0.3 |
| Potassium Chloride | 0.1 |
| Potassium Orthophosphate, mono-H | 0.5 |
| Magnesium Sulfate Heptahydrate | 0.5 |
| Ferrous Sulfate Heptahydrate | 45.0 |

F. Silica Gel Media

Three solutions were prepared. The first solution involved dissolving 10 of Silica Gel into 100 ml of 7% w/v KOH. The solution was stirred on a hot plate until the silica gel was dissolved. The opaque, light tan liquid was then autoclaved at 121° C./15 psi for 20 minutes. The liquor was clarified. The second solution was a double strength concentration of 9K. This solution was pH adjusted to 1.8 with 1.0N $H_2SO_4$ and then sterile filtered through a Gelman Acrodisc TM 0.2 $\mu$m membrane. The third 20% o-phosphoric acid solution was prepared by diluting 85% certified o-phosphoric acid with 0.2 $\mu$m purified water. This solution was also sterile filtered through a Gelman Acrodisc TM 0.2 $\mu$m membrane. The medium was readied by adding 20 ml of the double strength 9K to 20 ml of the silica gel/KOH solution. After this addition, the ferrous sulfate precipitated out of solution. Approximately 2.5 ml of the 20% o-phosphoric acid solution was then added until the pH adjusted to 7 0. Petri dishes were poured and allowed to solidify.

Plate and Broth Preparation

After autoclaving, the flasks were again placed on the Corning hot/stir plates and stirred. Petri dishes were then removed from sterile plastic holding sleeve(s) and stacked by fours. Approximately 15 to 20 ml of hot agar was poured into each dish as the lids of the dishes were quickly raised. The lids were then replaced. After pouring agar into all dishes, each plate lid was again raised while a Bunsen burner flame was passed quickly over each agar surface to pop any bubbles. The plates were then allowed to cool. After cooling and setting of the agar, the lids were lifted and the water on the inside was shaken off. The plates were then allowed to dry completely before inoculation or return to the plastic sleeves.

A 10 $\mu$l pre-sterilized Elkay (Fisher 13-075-1) plastic loop or a 10 ml sterile pipette was used for culture inoculation and streaking of flasks and petri dishes. In streaking, the loop was dipped into an inoculating broth culture which had been well-stirred. When the test involved a broth, the loop was placed in the liquid and shaken vigorously into the new medium whereas when the experiment involved petri dishes, the loop was drawn across or "streaked" through the sterile agar, along one side of the dish. Another streak was then made through the first streak with another clean, sterile loop. This loop was then rotated 180° exposing a sterile surface, and zig-zagged through the second streak. For inoculation, a similar technique was used.

Since a fungus contaminant was shown to inactivate ATCC 53921 at room temperature, the culture media may also contain antifungal agents to prevent growth of the fungus. Such agents are well known to those skilled in the art and include both fungicidal and fungistatic agents, including potassium iodide.

Additional details of the invention will appear from the Examples in conjunction with the Figures and the claims.

EXAMPLES

To test the capabilities of bacterial bioleaching of a selected metal from an integrated circuit containing the selected metal the following experiments were performed.

EXAMPLE A

Bioleaching of gallium and germanium is accomplished by seeding a bioreactor with 10% bacterial culture of ATCC 53921 acclimated on a 10% solids raw material input. A nutrient (9K) is added for initial growth. The chips for leaching are ground to between 20 and −400 mesh, and are placed within the nutrient solution. Reaction temperatures range from between 25° and 85° C., with an optimum temperature of about 62° C. to 72° C. Filtered deionized water (>0.2 microns), pH 1.8, is added to off-set evaporation. The treated solution is later analyzed for the presence of gallium and germanium, which are detected along with zinc, tin, lead and copper.

EXAMPLE B

Initial tests

Eight chips containing gallium arsenide weighing a total of 111 milligrams (mg) and free of any extraneous material were obtained.

The chips were triturated using a mortar and pestle before being transferred to a 250 milliliters (ml) titration flask. The flask was plugged with a foam plug and then sterilized at 15 pounds per square inch for 20 minutes (15#/20 min.). Two-hundred ml of Lundgren's 9K(9K) culture medium was transferred to the flask by sterile technique followed by inoculation.

The inoculum was prepared by centrifuging a sample of gallium-bioleaching bacteria for 10 minutes at 3300 rpm., re-suspending the slurry, and then inoculating the culture with 1 ml of this suspension. The inoculation was completed on the first day. Activity was checked on the second day and active bacteria were observed.

Activity was checked on day six through day nineteen and live bacteria were observed. The culture solution had become turbid. Observations using a "hanging drop" technique revealed that the bacteria were clustered around the chip fragments. The clustering of bacteria around chip fragments could not be observed using flat slides and cover glasses.

Bacterial activity was checked each work day on this culture with the following being noted: activity increased during the first two weeks of the culture life and then slowed down at 15 days. The bacteria remained alive and continued to multiply and grow, but very slowly. Activity started to increase on day 19. This activity increased on day 21 and continued doing so until day 40.

EXAMPLE C

Efforts to expand the tests of Example B were started on day 42 with the procurement of more chips from Tandy Electronics of Salt Lake City, Utah. The new chips were defective and were considered as "scrap" by Tandy. Scrap is defined as being chips structurally defective in their electronic configuration, or failing to meet design specifications for that product. Scrap chips are therefore not useful for further electronics manufacturing. Additionally, gallium arsenide of 6-9's (99.9999%) purity, Aesar, 12939b, and CAS 1303-00-0 were used.

Four tests were prepared as follows:

(1) 362 mg. of Aesar GaAs was triturated and transferred to a 250 ml flask as in the previous culture.

(2) Complete chips were broken in the mortar until no further trituration was possible. The resultant powder was transferred to a 250 ml flask. 2.306 grams(g) of material were obtained.

(3) Two chips were triturated and stripped for 10 minutes in 50% volume to volume (v/v) nitric acid followed by five rinses with tap water; 1.114 grams of material were obtained from 2.311 grams of chips before transferring to a flask.

(4) Eight chips were cut apart with diagonal pliers and broken so as to expose the actual chip. These were stripped 10 minutes in 50% v/v nitric acid and rinsed five times with tap water. Only the final weight of 1.242 was determined before transferring the material to a flask. Gold, silver, and chips were left after this treatment.

Each flask was plugged with a foam plug, sterilized at 15#/20 min. and cooled before adding 200 ml 9K medium. The flasks were inoculated on day one as before using the slurry containing bioleaching bacteria. A daily activity log was kept and the following noted: The culture receiving pure gallium arsenide was as active as the other culture (but not more so) with the bacterial clustering or "haloing" occurring 8 days after inoculation. Activity became very slow after 15 days. This culture (identified as #1) was sub-cultured into two cultures identified as 1a and 1b. Sub-culture 1a was prepared by triturating and transferring 492 mg of Aesar GaAs to a flask and sterilizing it. One hundred ml of 9K medium were added with ½ of the culture (well-stirred) and placed on the rotary shaker. Sub-culture 1b was prepared as for 1a, but 498 mg of Aesar GaAs were used and the culture was placed on a magnetic stirrer. Cultures Two and Three each received 500 mg of Aesar GaAs after it was sterilized. Activity in each culture rapidly increased and one could see the amount of GaAs in 1a and 1b decreasing rapidly. The culture on the stirrer was at least twice as active and GaAs degradation was several magnitudes more rapid.

A fungus of a deep purple-black color having very dense colonies on agar plates appeared on day 4 in culture Four (acid stripped chips cut apart, not triturated). This culture was terminated on day 27 after having been subcultured to test the capability of this fungus to degrade either chips or the phenolic insulator material surrounding the chips. Although small fragments of insulator and chips were enmassed within the fungal mycelia, no degradation of chips occurred and only slight surface etching of the insulator material was observed. This subculture was terminated 42 days after subculturing.

Culture Two was started using chips containing the complete "interconnects" (the metal contacts or pins from the chip that allow for contact with the circuit board) and culture Three had these nitric acid soluble metals removed. Activity was similar to the cultures receiving GaAs during early growth. This growth was maintained by adding 500 mg of Johnson - Mathey (Great Britain) (JM or Aesar) GaAs to each culture on day 15. Growth was becoming very slow by day 73. Growth was fast to begin with, then slowed.

Culture Two had a blue-green hue (most likely from dissolved copper interconnects).

Culture Three developed fungus contamination and changed color from the clear light greenish hue to a yellow-brown with slight turbidity.

Cultures 1a and 1b were still active after 94 days, and received additional feedings of chips or GaAs. Both received sterile chip material on days 15 and 78. 1a received 832 mg from 43 cut up chips and 1b received 719 mg of similar chip material. The gold wire and solder pads as well as crystalline silver was observed in 1b, but not in other cultures receiving fragmented chips. This is most likely due to a yellow granular or flaky coating that forms on the surfaces of the chip fragments and the flask surface. This material coated or mixed with most everything in the culture.

Five subcultures were established on two successive days. These cultures were numbered 7 through 11 and received 189, 398, 419, 209, and 404 mg of Aesar GaAs respectively. Culture Seven was inoculated from 1b, culture Eight from 2, culture Nine from 1a, and cultures Ten and Eleven were inoculated with 5 ml each from the "Gallium" culture. Cultures Ten and Eleven showed good activity while Seven, Eight and Nine were just becoming active.

A control was established using two chips in sterile 9K. After several days, no degradation of the chips was apparent, with the circuitry still intact and exposed GaAs still bright and shiny.

The following observations were made:

Chips are not degraded in 9K even with some agitation. The contaminant fungus did not degrade chips.

ATCC 53921 can remove Ga as GaAs from chips or in gallium's "free" elemental state. Once induced to degrade GaAs, the bacteria can effectively shorten the time to degrade GaAs several fold. The bacteria must receive regular feedings of GaAs containing materials in order to maintain active, functioning populations. Rapid agitation (as in magnetic bar stirring) increases GaAs degradation while rotary mixing as in the rotary shaker is much less effective. The presence of copper (as in Culture 2) appears to limit activity or viability of the bacteria which is quite unlike the effect of copper on *T. ferrooxidans*.

The bacteria seem to function well in the presence or absence of the phenolic chip insulation. The presence of gold or silver as solder constituents does not appear to have negative effects upon the bacteria. Tin overplate on the interconnects and pins is solubilized during the degradation process. The practice of using induced bacteria in establishing new cultures reduces degradation time from approximately 14 days to about 5 days in batch culture.

The silicon overlay or underlay on chips does not appear to be affected by bacterial degradation.

Complete chips with no fractures are only slowly degraded whereas finely triturated chips are rapidly degraded in the presence of bacteria. Reduction of chips to very small particles is therefore preferred in order to accelerate chip degradation.

Photomicrographs illustrate the intimate contact the bacteria exhibit while degrading chips. Masses of bacteria form on the chip surface. This latter aspect indicates degradation is exoenzymic which is typical of bacterial trophic functions.

Microscopic examination of cultures reveals the bacteria form "halo-like" masses around suitable solid substrates (chip fragments).

EXAMPLE D

A soil sample taken at a geothermal power plant is used to inoculate a medium (e.g. the previously described B. Nutrient Broth). The medium contains, dissolved therein, gallium arsenide (e.g. 5 weight percent) and is maintained at a temperature greater than 45° C. Mixed bacterial colonies are allowed to grow in this medium creating a mixed culture. This procedure preliminarily screens the mixed culture of bacteria and other microorganisms not able to withstand temperatures greater than 45° C. and concentrations of GaAs.

The mixed culture is then diluted with sterile water using sterile techniques. The dilution of mixed culture is then immediately used to inoculate a test tube containing a melted agar medium that has been cooled to 45° C. The test tube is then agitated to disperse the organisms throughout the medium before being poured into sterile petri dishes and allowed to solidify. Alternatively, a liquid nutrient broth or agar may be used. A culture from this method should result in evenly dispersed colonies. Dilutions must contain enough organisms to provide a number of separate colonies on each plate without covering the petri dish with colonies that have grown together which may require several different dilutions to be plated.

Each of the separate colonies is then tested for its ability to bioleach the desired metals from the integrated chips. Such testing may be done as previously described in Examples A-C, substituting the bacteria being tested for ATCC 53921.

While the invention has been specifically described herein with reference to bioleaching of valuable metals or metal compounds such as GaAs from integrated circuits, the invention may be used to leach gallium, germanium and gallium compounds from a conglomeration of materials, especially scrap manufactured components containing such metals as metallic compounds.

Reference to specific embodiments or examples are not intended to limit the scope of the appended claims.

What is claimed:

1. A method of leaching selected metal compounds from integrated circuits containing said metal compounds, said metal compounds having a metallic component selected from the group consisting of zinc, tin, lead, gallium, and germanium, said method comprising:
    placing said integrated circuits in an admixture of aerobic thermophilic bacteria and culture medium for sustaining the growth thereof at a temperature greater than 50 degrees centigrade for a sufficient amount of time to leach said metal compounds from said integrated circuits into said admixture, said aerobic thermophilic bacteria having deposit accession number ATCC 53921, being acidophilic and having an affinity for arsenic.

2. The method according to claim 1 wherein said integrated circuits are crushed before being placed into the culture medium containing bacteria.

3. The method according to claim 2 wherein said metallic component is germanium.

4. The method according to claim 2 wherein said integrated circuits are crushed to between 20 and −400 mesh.

5. The method according to claim 4 wherein the culture medium containing bacteria and crushed integrated circuits is maintained at a temperature of about 62 to about 72 degrees centigrade.

6. The method according to claim 5 further including infusing air through said culture medium, bacteria, and crushed integrated circuits.

7. A method of leaching gallium arsenide from integrated circuits containing gallium arsenide, said method comprising:
    placing the integrated circuits into an admixture of aerobic thermophilic bacteria having the ability to leach gallium arsenide from said integrated circuits and culture medium for sustaining the growth thereof for a sufficient amount of time to leach gallium arsenide from said integrated circuits, said aerobic thermophilic bacteria having deposit accession number ATCC 53921, being acidophilic and having an affinity for arsenic.

8. The method according to claim 7 further including crushing said integrated circuits before placing the integrated circuits into the culture medium containing bacteria.

9. The method according to claim 8 wherein the culture medium is 9K.

10. The method according to claim 9 wherein said integrated circuits are crushed to between about 20 and about −400 mesh.

* * * * *